(12) United States Patent
Clowers et al.

(10) Patent No.: US 7,560,688 B2
(45) Date of Patent: Jul. 14, 2009

(54) MASS ANALYSIS OF MOBILITY SELECTED ION POPULATIONS

(75) Inventors: Brian H. Clowers, Richland, WA (US);
Herbert H. Hill, Jr., Pullman, WA (US);
Prabha Dwivedi, Pullman, WA (US);
Matthew Pollard, Moscow, ID (US)

(73) Assignee: Washington State University, Pullman, WA (US)

( * ) Notice: Subject to any disclaimer, the term of this patent is extended or adjusted under 35 U.S.C. 154(b) by 424 days.

(21) Appl. No.: 11/582,198

(22) Filed: Oct. 16, 2006

(65) Prior Publication Data

US 2007/0158543 A1 Jul. 12, 2007

Related U.S. Application Data

(60) Provisional application No. 60/726,549, filed on Oct. 14, 2005.

(51) Int. Cl.
*H01J 49/00* (2006.01)
(52) U.S. Cl. .................. 250/287; 250/281; 250/282; 250/286; 250/288; 250/290; 250/292; 250/294
(58) Field of Classification Search .............. 250/281, 250/282, 286–288, 290, 292, 294
See application file for complete search history.

(56) References Cited

U.S. PATENT DOCUMENTS

| 5,905,258 | A  | * | 5/1999 | Clemmer et al. | 250/287 |
| 6,504,149 | B2 | * | 1/2003 | Guevremont et al. | 250/286 |
| 6,559,441 | B2 | * | 5/2003 | Clemmer | 250/287 |
| 7,077,944 | B2 | * | 7/2006 | Clemmer | 205/287 |

* cited by examiner

*Primary Examiner*—Jack I Berman
*Assistant Examiner*—Meenakshi S Sahu
(74) *Attorney, Agent, or Firm*—Barry L. Davison; Davis Wright Tremaine LLP (57) ABSTRACT

Particular aspects provide novel methods for analysis of ion populations, the methods comprising filtering and selecting an ion population using a low-field dual-gate ion mobility spectrometer comprising a drift tube, the spectrometer operating at a pressure of at least 100 Torr, to provide mobility-selected ions. Certain aspects comprise: (i) subsequently accumulating the low-field selected ions in an ion trap (e.g., an MS ion trap) and mass spectrometry analysis; (ii) introducing the low-field selected ions into a high-field ion mobility spectrometer for separating thereby (optionally followed by mass spectrometry); and (iii) introducing the low-field selected ions into an ion trap mass spectrometer, and subsequently into a second low-field ion mobility spectrometer (e.g., a non-dual gate spectrometer operating at less than about 100 Torr). Additional aspects provide novel apparatus and combination thereof for performing the disclosed methods.

66 Claims, 7 Drawing Sheets

MASS ANALYSIS OF MOBILITY SELECTED ION POPULATIONS

CROSS-REFERENCE TO RELATED APPLICATIONS

This application claims the benefit of priority to U.S. Provisional Patent Application 60/726,549 filed Oct. 14, 2005 and entitled "Mass Analysis of Mobility Selected Ion Populations Using Dual Gate Ion Mobility Quadrupole Ion Trap Mass Spectrometry," which is incorporated by reference herein in its entirety.

FIELD OF THE INVENTION

Particular aspects of the present invention relate to novel methods and apparatus, and novel combinations thereof, having substantial utility for characterization of ions (e.g., gas-phase ions).

BACKGROUND OF THE INVENTION

The mating of orthogonal, or complementary, methods of separating analytes of interest is of fundamental importance to the advancement of the study of highly complex systems. Such matings are commonplace in the art, however for each combination and respective order thereof, specific attributes are required of the mated instruments. Herein methodology for novel matings of analytical instrumentation are described.

Traditionally, ion mobility spectrometry (IMS) has been used for the analysis of gas phase compounds (Hill et al., *Anal. Chem.* 62(23):1201A, 1990; Eiceman and Karpas, *Ion Mobility Spectrometry*, CRC Press, New York, N.Y., p. 1-15, 1994). Moreover, with the advent of electrospray ionization (ESI) (Fenn et al., *Science* 246(4926):64-71, 1989), and matrix-assisted laser desorption ionization (MALDI) (Tanaka et al., *Rapid Comm. In Mass Spec.* 2(8):151-153, 1988; Karas and Hillenkamp, *Anal. Chem.* 60(20):2299-2301, 1988) the scope of IMS analysis has greatly expanded (Shumate, et al., *Anal. Chem.* 61:601-606, 1989; Helden et al., *Science* 267:1483-1485, 1995; Khalid, et al., *Rapid Commun. In Mass Spectrometry*, 17, 87-96, 2003).

In the presence of a neutral drift gas, IMS separates gas phase ions based upon their differential migration through a weak homogeneous electric field (Revercomb and Mason, *Anal Chem.* 47(7):970-983, 1975). In cases where the analyte ions are much larger than the drift gas molecule, an ion's mobility is proportional to its collision cross section, $\Omega$, and charge, z. In these traditional 'low-field' applications a typical analyte resident time within a drift tube is on the order of ten's of milliseconds.

Newer implementations employ high-field IMS ('high-field' asymmetric waveform ion mobility spectrometry, FAIMS, or differential mobility spectrometry, DMS collectively referred to hereinafter as 'High-Field' IMS), the ions are separated on their interaction in a rapidly switched high and low electric field. In high-field IMS, the ions are pneumatically moved through a switching electric field which is orthogonal to the pneumatic flow. Under the high-field condition (~10,000 V/cm) the ions are rapidly accelerated for a short time-constant toward the respective positive or negative electrode. After a few hundred nanoseconds, the high electric field is reversed to a low electric field of opposite polarity for twice the time-constant, forcing the ions to change their direction. Without further assistance, the ion's trajectory would have them collide with an electrode and never exit the system. Therefore, akin to the DC offset in a quadrupole mass spectrometer, the zero-crossing point of the switching voltages is slowly changed, or compensated, incrementally allowing ions to exit the system, yielding a compensation-voltage-dependent ion mobility spectrum. Even though the resulting spectrum is a function of the compensation voltage, separation occurs based on the difference of their response in the high and low electric fields. Within these high-field applications a typical analyte resident time within a drift tube is on the order of hundreds of milliseconds.

Since the high-and low-field techniques separate ions differently, it would naturally be beneficial to couple the instruments as has been successfully implemented in the art. The output from a high-field ion mobility spectrometer was directed to the input of a low-field ion mobility spectrometer instrument (Tang et al., *Anal. Chem.* 77:6381-6388, 2005). When coupling the low-field (and much faster) instrument to the output of the high-field (and slower) instrument, multiple low-field IMS scans can be performed in the time it takes for the ions to traverse the high-field system. Significantly, due to the discrepancies with the residence times, coupling the instruments in the reverse order (low-field output into high-field input) will cause loss of resolution from the low-field IMS. Since the low-field device processes analytes more rapidly the separation afforded by the low-field device will be undone by the backlog created at the entrance of the high-field device.

Another desirable combination of instrumentation is provided by the coupling of IMS instrumentation to mass spectrometers (MS). The IMS concept of measuring size-to-charge ratio is complementary to the principle of measurement in mass spectrometry (MS) of mass-to-charge ratio (m/z). When combined, ion mobility-mass spectrometry (IMMS or IM:MS) represents a powerful analytical combination capable of distinguishing ions based upon both size and mass to charge ratios. This union has provided an added degree of specificity above that attainable by mass spectrometry alone. While low pressure, low-field IMMS systems have been described in the art, (Clemmer, U.S. Pat. No. 6,559,441, Clemmer, U.S. Pat. No. 7,077,944, and Clemmer, U.S. Pat. No. 5,905,258) these systems employ MS methods (e.g., TOF-MS) wherein the timescale of MS sampling is much faster than the transit time of an analyte through the low-field IMS drift tube. These implementations highlight the larger problem one faces when attempting to couple orthogonal methods of analytical characterization: In order to obtain meaningful separations and characterizations, the timescale of the first method must be slower than the timescale of the second. High-field IMMS couplings are also common in the art and generally do not suffer from such timing problems. (Guevremont, et al. U.S. Pat. No. 6,504,149; Purves et al. Review of Scientific Instruments 69 (12):4094-4105, 1998).

While MS alone has achieved resolution (m/$\Delta m_{50\%}$) measurements of over 400,000 (Bossio et al., *Anal. Chem.* 74(7): 1674-1679, 2002), routine differentiation between isomeric species using mass spectrometry has proven elusive. Often distinguishing features for a particular isomer require complex multidimentional mass spectroscopic (MS$^n$) experiments where the measurement of relative peaks heights is necessary for identification (Tao et al., *J. Am. Chem. Soc.* 122(43):10598-10609, 2000; Leavell et al., *J. Am. Soc. Mass Spectrom.* 14(4):323-331, 2003). Because IMS can separate analytes based on their size to charge ratio, low-field IMMS has been employed to differentiate between isomeric species, IMMS experiments have demonstrated the ability to conclusively identify isomeric species (Wu et al., *Anal. Chem.*

72:391-395, 2000; Srebalus-Barnes et al., *Anal. Chem.* 74:26-36, 2002; Clowers et al., *J. Am. Soc. Mass Spectrom.* 16(5):660-669, 2005).

Hybrid low-field IMMS instruments have also been used to obtain conformational information for proteins (Sowell et al., *J. Am. Soc. Mass Spectrom.* 15:1341-1353, 2004; Ruotolo et al., *Int. J. Mass Spec.* 219(1):253-267, 2002; Bernstein et al., *J. Am. Chem. Soc.* 127:2075-2084, 2005), peptides (Srebalus-Barnes et al., *Anal. Chem.* 74:26-36, 2002; Hill et al., *Int. J. Mass Spec.* 219(1):23-37, 2002; Ruotolo et al., *J. Prot. Res.* 1(4):303-306, 2002; Barran et al., *Int. J. Mass Spec.* 240(3): 274-284, 2005; Breaux and Jarrold, *J. Am. Chem. Soc.* 125: 10740-10747, 2003), carbohydrates (Clowers et al., *J. Am. Soc. Mass Spectrom.* 16(5):660-669, 2005; Lee et al., *J. Mass Spec. Ion Proc.* 167/168:605-614, 1997; Leavell et al., *J. Am. Soc. for Mass Spec.* 13(3):284-293, 2002) and other biologically relevant system (Wyttenbach et al., *Int. J. Mass Spec.* 193:143-152, 1999; Koomen et al., *Anal. Bioanal. Chem.* 373(7):612-617, 2002; Gidden et al., *Int. J. Mass Spec.* 240: 183-193, 2005; Matz et al., *Anal. Chem.* 73(8):1664-1669, 2001).

Mass spectrometry techniques that have successfully been interfaced with low-field ion mobility include: quadrupole (QMS), (Karasek et al., *Anal. Chem.* 48(8):1133-1137, 1976; Liu et al., *Anal. Chem.* 69:728A, 1997; Wyttenbach et al., *Int. J. Mass Spec.* 212:13, 2001; Hudgins et al., *Int. J. Mass Spec. Ion Proc.* 165/166:497-507, 1997; Wu et al., *Anal. Chem.* 70(23):4929-4938, 1998), time-of-flight (TOF) (Ruotolo et al., *Int. J. Mass Spec.* 219(1):253-267, 2002; Steiner et al., *Rapid Comm. In Mass Spec.* 15(23):2221-2226, 2001; Hoaglund et al., *Anal. Chem.* 70:2236-2242, 1998), quadrupole ion trap (QIT), (Liu et al., *Anal. Chem.* 69:728A, 1997; Creaser et al., *Anal. Chem.* 72(13):2724-2729, 2000), linear ion trap (LIT), (Sowell et al., *J. Am. Soc. Mass Spectrom.* 15:1341-1353, 2004), and *Fourier transform ion cyclotron resonance* (FT-ICR) *mass spectrometers* (Creaser et al., *Anal. Chem.* 72(13):2724-2729, 2000).

Typically, mass analysis is performed after an ion mobility separation. However, in some implementations the ability of QIT and LIT MS to trap and concentrate ions have been utilized as an ion mobility injection mechanism within low-field IMS instruments operating under near vacuum conditions (Liu et al., *Anal. Chem.* 69:728A, 1997; Creaser et al., *Anal. Chem.* 72(13):2724-2729, 2000; Sowell et al., *J. Am. Soc. Mass Spectrom.* 15:1341-1353, 2004). This union allows for higher IMS duty cycles to be achieved along with MS/MS experiments prior to mobility separation.

However, because of the vacuum requirement of ion trapping methodologies for concentrating ions prior to mobility analysis, these instruments have only been realized using low pressure (1-100 Torr) ion mobility analysis. Since IMS achieves a better resolution at higher pressures, IMMS systems employing a high pressure in the IMS segment are generally more desirable. Higher pressure IMMS have only been obtained using QMS (Karasek et al., *Anal. Chem.* 48(8): 1133-1137, 1976; Wu et al., *Anal. Chem.* 70(23):4929-4938, 1998; Dugourd et al., *Rev. Sci. Instrum.* 68:1122-1129, 1997) and TOF (Steiner et al., *Rapid Comm. in Mass Spec.* 15(23): 2221-2226, 2001) systems. The disadvantage to these instrumental configurations has been their inability to provide the valuable fragmentation information from $MS^n$ analyses.

Conventionally, a successful low-field IMMS instrument utilizes a mass analysis method capable of obtaining m/z information on a time scale much faster than the common signal averaged IMS experiment; however, this has not always been the case. Early IMMS unions used boxcar averaging with a mobility scanning technique that required two ion gates working in tandem to selectively filter ions for mass analysis (Karasek et al., *Anal. Chem.* 48(8):1133-1137, 1976). Despite being significantly slower than current methods, this ion mobility filtration technique has recently been reexamined, wherein a scanning ion mobility spectrometer was interfaced with a triple quadrupole mass spectrometer (Sysoev et al., *Rapid Comm. in Mass Spec.* 18(24):3131-3139, 2004). Using this technique it was possible to selectively filter ions prior to mass analysis, however, the nature of the experiment and approach excluded and precluded the possibility of collection of $MS^n$ data on low abundance analytes because, as appreciated and disclosed herein below by the present Applicant, there is no mechanism for the selective sequestration and fragmentation of analytes of interest. Moreover, the serial nature of the sampling results in an undesirably high MS duty cycle Therefore, the art described above demonstrates the significant need for the development of novel and versatile platforms for multidimensional analytical separations that appreciate and incorporate elements for proper mating of process timescales.

SUMMARY OF THE INVENTION

Particular aspects provide a method for analysis of ion populations, comprising: filtering and selecting an ion population or portions thereof using a dual-gate low-field ion mobility spectrometer comprising a drift tube, the spectrometer operating at atmospheric pressure or higher pressure, wherein, the dual-gate ion mobility spectrometer comprises two gates and controlling means to enable the gates to work in tandem to select ion populations based upon their drift times. In certain aspects, the parameters settable by the controlling means are selected from the group consisting of: a first ion gate pulse width; a scan window governing a second ion gate pulse delay and width, a scan range, a number of ion gate pulses per injection cycle, and combinations thereof. In certain implementations the selected ion population may be introduced into a high-field ion mobility spectrometer in operative communication with the low-field ion mobility spectrometer; comprising a drift tube with the high-field spectrometer operating at atmospheric pressure or higher pressure, the output of the high-field mobility spectrometer may optionally be introduced into a mass spectrometer in operative communication with the high-field ion mobility spectrometer. In yet other implementations, a plurality of mobility-selected ion pulses originating from the dual-gate low field ion mobility spectrometer; are accumulated, during an ion trap injection cycle, such embodiments including, for example, wherein the plurality of mobility-selected ion pulses are accumulated in an ion trap of a mass spectrometer, the ion trap in operative communication with the low-field ion mobility spectrometer; and, for example, analyzing the accumulated mobility-selected ions by mass spectrometry.

In particular embodiments, separating and filtering the ion population, or portions thereof, using the dual-gate ion mobility spectrometer comprises operative coordination of one or more settable parameters selected from the group consisting of: a first ion gate pulse width; a scan window governing a second ion gate pulse delay and width, a scan range, an ion trap injection cycle time, and a number of ion gate pulses per ion trap injection cycle. In particular embodiments, the method further comprises, prior to separating and filtering the ion population, determining a drift time for a desired ion or ion population.

In particular embodiments, obtaining an ion population comprises use of an electrospray ionization (ESI) unit. In preferred aspects, the electrospray ionization unit is positioned off-axis with respect to the axis of the drift tube of the dual-gate ion mobility spectrometer. Preferably, the off-axis orientation is about 45 degrees off the axis of the drift tube. While an ESI source has been employed herein, other API methods, including but not limited to radioactive source, corona discharge ionization, and atmospheric pressure photoionization, could also be applied.

The inventive methods are applicable in a positive or negative mode, for filtering and selecting positive ions or negative ions, respectively.

Additional aspects provide a method of analysis of ion populations, comprising: separating ions using low-field ion mobility spectrometry at atmospheric pressure or higher pressure; filtering the ions to select specific ions; further analyzing the selected ions using a high-field ion mobility spectrometer.

Yet further aspects provide an apparatus for analysis of ion populations, comprising: a dual-gate low-field ion mobility spectrometer comprising a drift tube, two gates and controlling means to enable the gates to work in tandem to select ion populations based upon their drift times, the spectrometer suitable to operate at atmospheric pressure or higher pressure to filter and select an ion population to provide for mobility-selected ions; a high-field ion mobility spectrometer operative with the low-field ion mobility spectrometer to further separate ions therefrom; and a mass spectrometer in operative communication with the high-field ion mobility spectrometer. In preferred aspects, the mass spectrometer is selected for the group comprising: Single, double or triple Quadrapole, Quadropole Ion Trap (QIT), Linear Ion Trap (LIT), fourier transform mass spectrometer (FTMS), Time of Flight (TOF). In particular aspects, the apparatus further comprises an electrospray ionization (ESI) unit suitable in operation to provide for an ion population. In particular embodiments, the electrospray ionization unit is positionable off-axis with respect to the axis of the drift tube of the dual-gate ion mobility spectrometer. Preferably, the electrospray ionization unit is positionable at about 45 degrees off the axis of the drift tube. In particular aspects, the parameters settable by the controlling means are selected from the group consisting of: a first ion gate pulse width; a scan window governing a second ion gate pulse delay and width, a scan range and combinations thereof. Preferably, the inventive apparatus comprises software and electronic means operative therewith for determining ion drift time by using a DGS mode (as defined herein), and for filtering ions, based on the drift time, using a SMM mode (as defined herein).

Additional aspects provide a method of analysis of ion populations, comprising: separating ions using low-field ion mobility spectrometry at atmospheric pressure or higher pressure; filtering the ions to select specific ions; accumulating the selected ions in an accumulation means; and analyzing the accumulated ions by mass spectrometry and or ion mobility means.

Yet further aspects provide an apparatus for analysis of ion populations, comprising: a dual-gate low-field ion mobility spectrometer comprising a drift tube, two gates (e.g., Bradbury Nielson type) and controlling means to enable the gates to work in tandem to select ion populations based upon their drift times, the spectrometer suitable to operate at atmospheric pressure or higher pressure to filter and select an ion population to provide for mobility-selected ions; an ion trap operative with the ion mobility spectrometer to accumulate ions therefrom; and a mass spectrometer in operative communication with the ion trap. Additional aspects provide a second low field ion mobility spectrometer in operative communication with the ion trap wherein ions collected within the trap may be injected into the low field IMS. In particular aspects, the ion trap is selected from the group consisting of a quadrupole ion trap (QIT), and linear ion trap (LIT) or ion cyclotron resonance (ICR) cell. In particular aspects, the apparatus further comprises an electrospray ionization (ESI) unit suitable in operation to provide for an ion population. In particular embodiments, the electrospray ionization unit is positionable off-axis with respect to the axis of the drift tube of the dual-gate ion mobility spectrometer. In particular embodiments, the electrospray ionization unit is positionable at about 45 degrees off the axis of the drift tube. In particular aspects, the parameters settable by the controlling means are selected from the group consisting of: a first ion gate pulse width; a scan window governing a second ion gate pulse delay and width, a scan range, an ion trap injection cycle time, a number of ion gate pulses per ion trap injection cycle, and combinations thereof. Preferably, the inventive apparatus comprises software and electronic means operative therewith for determining ion drift time by using a DGS mode (as defined herein), and for filtering ions, based on the drift time, using a SMM mode (as defined herein).

Particular preferred aspects provide novel methods for analysis of ion populations, the methods comprising filtering and selecting an ion population using a low-field dual-gate ion mobility spectrometer comprising a drift tube, the spectrometer operating at a pressure of at least 100 Torr, to provide mobility-selected ions. Certain aspects comprise: (i) subsequently accumulating the low-field selected ions in an ion trap (e.g., an MS ion trap) and mass spectrometry analysis; (ii) introducing the low-field selected ions into a high-field ion mobility spectrometer for separating thereby (optionally followed by mass spectrometry); and (iii) introducing the low-field selected ions into an ion trap mass spectrometer, and subsequently into a second low-field ion mobility spectrometer (e.g., a non-dual gate spectrometer operating at less than about 100 Torr). Additional aspects provide novel apparatus and combination thereof for performing the disclosed methods.

Certain aspects provide a method for analysis of ion populations, comprising: obtaining an ion population; filtering and selecting the ion population or portions thereof using a low-field dual-gate low-field ion mobility spectrometer comprising a drift tube, the spectrometer operating at a pressure of at least 100 Torr, to provide for at least one low-field mobility-selected ion pulse; accumulating, during an ion trap injection cycle, the at least one mobility-selected ion pulse in an ion trap of a mass spectrometer, the ion trap in operative communication with the ion mobility spectrometer; and analyzing the accumulated mobility-selected ions by mass spectrometry.

Additional aspects provide a method for analysis of ion populations, comprising: obtaining an ion population; filtering and selecting the ion population or portions thereof using a dual-gate low-field ion mobility spectrometer comprising a drift tube, the spectrometer operating at least 100 Torr, to provide for at least one low-field mobility-selected ion pulse; introducing, during at least one introduction cycle, the at least one mobility-selected ion pulse into an ion-receiving portion of a high-field ion mobility spectrometer in operative communication with the low-field ion mobility spectrometer; and separating the introduced mobility-selected ions by high-filed ion mobility spectrometry to provide for high-field mobility selected ion populations. Certain aspects comprise introducing, prior to introducing the plurality of high-field mobility-selected ion populations into an ion-receiving portion of a mass spectrometer, accumulating, during an ion trap injection cycle, the plurality of high-field mobility-selected ion populations in an ion trap of a mass spectrometer, the ion trap in operative communication with the high-field ion mobility spectrometer.

Yet additional aspects provide a method for analysis of ion populations, comprising: obtaining an ion population; filtering and selecting the ion population or portions thereof using a first dual-gate low-field ion mobility spectrometer comprising a drift tube, the spectrometer operating at a pressure of at least 100 Torr, to provide at least one low-field mobility-selected ion pulse; and accumulating, during an ion trap injection cycle, a plurality of low-field mobility-selected ion pulses in an ion trap, the ion trap in operative communication with the output of the low-field ion mobility spectrometer to provide for selected accumulated ions. Particular aspects further comprise introducing the selected accumulated ions into an ion-receiving portion of a second low-field ion mobility spectrometer in operative communication with the ion trap; and separating the introduced selected accumulated ions by further low-field ion mobility spectrometry to provide for further mobility selected ions. In particular embodiments, the second low-field ion mobility spectrometer is a non-dual gate spectrometer operating at less than about 100 Torr.

Further aspects provide an apparatus for analysis of ion populations, comprising: a dual-gate low-field ion mobility spectrometer comprising a drift tube, two ion gates and controlling means to enable the gates to work in tandem to select ion populations based upon their drift times, the spectrometer suitable to operate at a pressure of at least 100 Torr to filter and select an ion populations to provide for mobility-selected ions; and an ion trap mass spectrometer, or a high-field ion mobility spectrometer, in operative communication with the dual gate low-field ion mobility spectrometer to further filter and select ion populations. In particular aspects, the high field ion mobility spectrometer is that of a FAIMS system. Certain aspects that comprise a high-field ion mobility spectrometer (e.g., FAIMS system), further comprise a mass spectrometer in operative communication with the output of the high-field ion mobility spectrometer to further filter and select ion populations. Certain aspects that comprise an ion trap mass spectrometer further comprise a low-field ion mobility spectrometer in operative communication with the output of the ion trap mass spectrometer to further filter and select ion populations.

DETAILED DESCRIPTION OF THE INVENTION

Employing a dual-gate ion filtering method, novel and substantially useful combinations of analytical separation dimensions are enabled herein. The dual gate method allows for selective injection of gaseous ion packets into subsequent stages of separation and/or analysis. This method removes the restrictions imposed by the differing instrumental resident times, thereby providing methods through which a fast method (e.g. low-field IMS) can be effectively mated with a relatively slow method (e.g. high-field IMS, Quadropole Ion Trap (QIT), Linear Ion Trap (LIT), fourier transform mass spectrometer (FTMS)).

Ionization methods. Particular exemplary embodiments provided herein utilize the electrospray ionization (ESI) source shown in FIG. 1, which was constructed at Washington State University out of PTFE Teflon™ and served to hold a 13 cm long fused silica, polyimide capillary (Polymicro Technologies, Phoenix, Ariz.) although it is to be understood that any of the ionization methods commonly utilized in the art may be substituted. For example, while an ESI source has been employed herein, other API methods, including but not limited to radioactive source, corona discharge ionization, and atmospheric pressure photoionization, etc., could also be applied. The electrical connection of ±12.5 kV was applied to the sample solution through a zero-dead volume stainless steel union (Valco Instruments Co. Inc., Houston, Tex.). Sample solutions for both the positive and negative mode were infused at a rate of 2 μL/min. Traditionally, the electrospray units used with IMS employ a target screen and have been oriented with the axis of the drift tube (Wu et al., *Anal. Chem.* 70(23):4929-4938, 1998; Steiner et al., *Rapid Comm. in Mass Spec.* 15(23):2221-2226, 2001). While still employing the target screen, the electrospray unit for the described instrument was oriented ~45° off the axis of the drift tube in order to avoid the occurrence of gate leakage due to incomplete desolvation.

Figure 1:
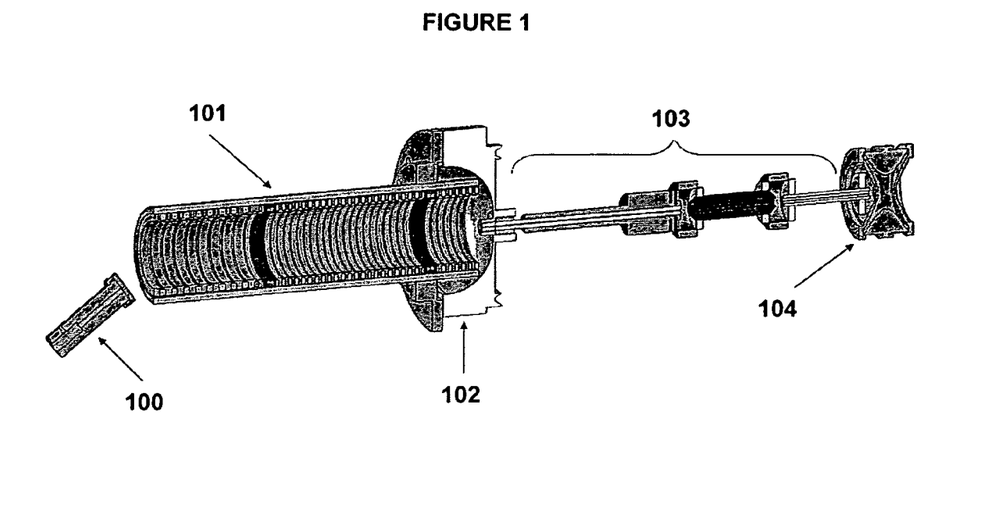
FIG. 1 shows, according to particular exemplary embodiments, a schematic of an embodiment of an Electrospray Ionization-Atmospheric Pressure-Dual Gate Ion Mobility-Quadrupole Ion Trap Mass Spectrometer. This instrument is comprised of six primary units: an electrospray ionization source (100); an ion mobility spectrometer (101); a spray shield and ion trap interface (102); ion guides and lenses (103); a quadrupole ion trap (104), and a PC based data acquisition system (not shown).
Figure 2:
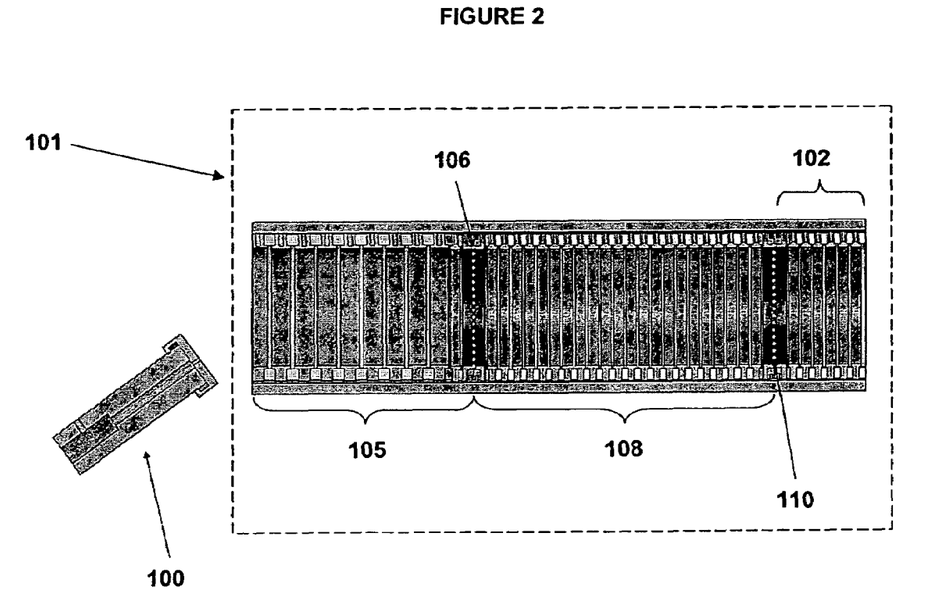
FIG. 2 shows, according to particular exemplary embodiments, a detailed representation of a representative dual gate ion mobility spectrometer comprising the following units: an electrospray source (100) and an ion mobility spectrometer (101), with the ion mobility spectrometer comprising a heated desolvation region (105), a first ion gate (106), a drift region (108), a second ion gate (110), and an ion trap interface (102). The two ion gates (e.g., Bradbury-Nielsen ion gates) work in tandem to select ion populations based upon their drift times for entrance into, for example, an ion trap (e.g., a quadrupole ion trap 104).

The atmospheric pressure low-field ion mobility spectrometer used for these studies was designed and constructed at Washington State University. This instrument employed a stacked ring design consisting of alternating conductive stainless steel and insulating alumina rings. As shown in FIGS. 1 and 2, differing sets of conducting drift rings were used throughout the IMS tube with the wider rings (6×47 mm, width and i.d., respectively) being employed for the desolvation region (105) and the thinner conducting rings (4.25×47 mm, width and i.d., respectively) utilized for the drift region (108) and ion trap interface (102 in FIGS. 1 and 2). Electrical contact between conducting drift rings was accomplished using a series of 500 kΩ and 1 MΩ resistors (Caddock Electronics Inc., Riverside, Calif.) with the lower valued resistors applied to the desolvation region. The potential applied to the tube totaled 9.5 kV with an effective drift region electric field of ~395 V/cm. It should be noted that the electric field was determined based upon the potential applied between ion gates and not the total applied voltage. Separating the 17.6 cm drift region from the desolvation region and low voltage IMS output interface were two ion gates (Wu, C. et al., *Anal. Chem.*, 70(23), 4929-4938, 1988). These two exemplary gates, labeled 106 and 110 in FIG. 2, consist of electrically isolated alternating sets of Alloy 46 wires (California Fine Wire Co., Grover Beach, Calif.) spaced 0.65 mm apart. The gates may, for example, comprise at least one of; Tyndall, Bradbury-Neilsen, or an electric potential well created by a reversible short between two electrodes within the chamber or various combinations thereof. In alternative modes of operation a short pulse of ions from an ionization source may be substituted for the entrance gate. In such implementations, the timing between the ion pulse and opening of the exit gate can be utilized as the gate delay. When open, the potential on the differing wire sets of the ion gates was equal to that of the reference potential. When closed the potential difference between wire sets was ~100 V with respect to the reference potential. It is to be understood that reasonable variations of the aforementioned variables as are known to those skilled in the art are considered to be encompassed by aspects of the present description and invention.

Also designed and assemble at Washington State University, the gate pulsing electronics record the referenced ion gate potential and output the user defined potential and pulsing profile necessary to modulate the ion gate. The reference voltage of each ion gate was determined by its spatial position in relation to the electric field of the drift tube. The desolvation of ions may be aided by a constant counter current flow between 0.1-10 L/min of gas held at 50-500° C. Any gas (or mixtures thereof) suitable for use in an IMS instrument may be utilized in practice of aspects of the invention, including but not limited to Nitrogen, Carbon Dioxide, Oxygen, Nitrous Oxide, Noble Gasses, Sulfur hexafluoride, and combinations thereof. In particular aspects, this desolvating drift gas was introduced by transmitting gas through a hollow drift ring possessing radially distributed apertures located towards the end of the drift tube. The ambient pressure in Pullman, Wash. ranged from 690-710 Torr throughout the described experiments.

The two gates open in series wherein a time delay between the opening of the entrance gate and opening of the exit gate is employed to selectively release a pulse of ions into a second dimension of separation and/or analysis. Such time delay may be static or dynamic throughout the course of a sample analysis. The function of such a gating method within the present invention is to remove the temporal problems associated with mating the fast, low resolution low-field IMS with the slow, higher resolution methods such as high-field IMS, or MS" methods.

LF-IMS:HF-IMS. In one implementation the output from the dual gate low-field IMS is coupled to a high-field IMS. An Electrospray ionization source (ESI) was operated at 15,000V which generated gaseous ions at the entrance to the low-field IMS. The high-voltage end of the low-field drift tube was 12,000V and the low voltage end was 2,000V. In this implementation, both the curtain gas from the high-field IMS and gas introduced through the hollow drift ring possessing radially distributed apertures located towards the end of the drift tube were utilized as a drift gas. As described above, the physical composition, flow rate and temperature of the drift gas can be modulated. The output from the low-field IMS can be mated directly to the input of a high-field IMS. A particular embodiment involves the use of an unmodified Ionalytics (FAIMS) system operated at a nominal 4000V dispersion voltage, ±1000V curtain plate voltage, ±35V outer bias voltage, with a 1:1 ratio of $He:N_2$ at 2 L/min. The curtain gas employed herein may provide the drift gas for both instruments, removing the second gas input employed within the low-field IMS, and here again any suitable gas or mixture thereof may be employed. It is to be understood that, based on the instant teachings, reasonable variations of the aforementioned variables will be recognized to those skilled in the art and are considered to be encompassed by the preceding description.

LF-IMS:HP-IMS:MS. The above-described mating can be utilized as a two-stage instrument (low field IMS-high field IMS) or the output from the second stage (the high field IMS) may be coupled to a third-stage of analysis. Particular embodiments involve the coupling of the low-field IMS:high-field IMS system to that of a mass spectrometer. In such embodiments, the low-field IMS:high-field IMS may operate in any one of three different modes: 1) a "pass through mode" wherein a static voltage drop throughout both IMS segments acts to completely remove water clusters and thoroughly desolvate gaseous analytes, and this mode of operation provides better signal to noise within the MS spectrum; 2) a "no gate" mode of operation wherein the low-field IMS solely serves as an extended desolvation region. In this mode of operation the separation provided by the low-field IMS is negated by the backlog created at the entrance to the high-field IMS, however the gaseous ions are more thoroughly desolvated, thereby providing better separation within the high-field IMS (In implementations wherein a researcher is attempting to isolate and pass only a specific analyte to a subsequent stage of analysis, this mode can be utilized to identify the optimal compensation voltage to employ within the high-field IMS to selectively pass only the analyte of interest); and 3) the "dual gate" mode of operation providing separation and selective release within the low-field IMS, a second, orthogonal mode of separation of the mobility selected ions within the high-field IMS and a third orthogonal mode of separation within the MS.

System Optimization. Within implementations utilizing an ion trap mass spectrometer as a third stage of analysis, a user may employ one or more of these modes of operation in the process of characterizing an analyte of interest. For example, one may wish to employ the no-gate mode of operation to identify the proper compensation voltage at which the analyte of interest is passed through the high-field IMS. Once the proper compensation voltage is identified, the dual-gate mode of operation is utilized wherein the delay time between the gate openings is swept in order to identify the optimal gate timing on the low-field IMS. Once both parameters have been identified, utilizing the dual-gate mode of operation both the delay time and compensation voltage can be held at said values to allow passage of only the analyte of interest to the ion trap.

In implementations wherein a non-ion trapping mass spectrometer is utilized as a third stage of analysis, any one of the three modes of operation may be employed. However in the dual-gate mode of operation, the mass spectrometer operates to continuously sample the output from the high-field IMS throughout a sweep of the compensation voltage. In such implementations the gate delay timing within the low-field IMS is held static during the sweep of the compensation voltage within the high-field IMS then stepped to a different gate delay and the process is repeated. Alterations to this process may be implemented to allow for signal averaging and other related methods to improve the signal-to-noise ratio.

In one implementation of such a mating, the output from the high-field IMS segment is coupled to a Thermo Electron LCQ Deca quadrupole ion trap mass spectrometer. In this implementation, the pressure drop associated with the entrance to the MS instrument drives both the flow of the drift gas and the analytes through the high-field IMS. As a result any one of many suitable fittings may be employed to mate the output of the high-field instrument to the input of the MS segment. In particular embodiments, the regulation of pressure at the entrance to the MS may be utilized to alter the flow rate of the drift gas through the high-field IMS, thereby influencing the separation afforded by this segment. Similarly, the nature of the fitting that couples the instruments may also be altered to influence the pressure drop at the high-field IMS-MS interface. It is to be understood that according to various aspects of the present invention, the low-field IMS:high-field IMS system could be mated to any type of mass spectrometer, including but not limited to single, double or triple Quadrupole, Quadrupole Ion Trap (QIT), Linear Ion Trap (LIT), fourier transform mass spectrometer (FTMS), Time of Flight (TOF).

LF-IMS:QIT-MS. Utilizing a similar strategy the dual gate low-field IMS has been mated to a QIT mass spectrometer. Within this implementation, the ions selectively released from the low-field IMS can be accumulated within an ion trap by collecting a plurality of ion pulses. Since the low-field IMS is operable to cycle through scans on the order of tens of milliseconds, if the gate timing were to remain static a plurality of mobility selected ion packets containing the same analytes can be collected and concentrated in the ion trap. Because the IMS is only transferring ions of interest to the ion trap, the temporal restrictions associated with the mating of IMS to QIT are avoided.

An electrospray ionization-dual gate-ion mobility-quadrupole ion trap mass spectrometer (ESI-DG-IMS-QIT-MS) was constructed to select mobility filtered ions prior to mass analysis. The instrument was assembled by coupling an atmospheric pressure mobility filtration technique with QIT. Using this high pressure gas phase separation technique, it was possible to selectively accumulate ions based upon their mobility prior to $MS^n$ fragmentation. This analysis technique provides the opportunity to gain additional insight into the chemistries of gas phase ions.

The atmospheric pressure ion mobility spectrometer described in this implementation was interfaced to an unmodified LCQ Deca quadrupole ion trap (QIT) mass spectrometer (Thermo Electron, San Jose, Calif.). Given the nature of the dual gate ion mobility filtration experiment, once ions exited the second gate the separation was effectively completed, however an electric field free of defects was still necessary to efficiently transmit the mobility selected ions towards the transfer capillary. The post-ion mobility analysis drift region or ion trap interface (#3 in FIGS. 1 and 2) was 3.7 cm in length and terminated against the ion trap spray shield. The heated transfer capillary used for ion transmission into the quadrupole ion trap MS was located ~3 mm from the end of the heated drift region and was held at 185° C. It is to be understood that variations in the temperature, distance and method for ion shuttling that are suitable and appropriate to the disclosed goals and implementations are also contemplated and within the scope of the present invention.

For the exemplary examples and implementations provided herein, the potential applied to the heated transfer capillary and ion optics varied between the positive and negative modes of operation. The respective values for the positive and negative modes of operation were as follows: transfer capillary (9.1 V, 3.0 V); multipole #1 offset (−5.4 V, 8.2 V); lens voltage (−67.5 V, 61.7 V); multipole #2 offset (−11.5 V, 12.7 V); entrance lens (−52.9 V, 56.6 V); ion trap offset (−10 V, 9.8 V); dynode (−14.9 kV, −0.07 kV); multiplier (−1090.7 V, −3.2 V). These values, along with the ion mobility operating parameters for the examples provided herein are summarized in TABLE 1. It is to be understood that reasonable variations of the aforementioned variables as are known or reasonably discoverable to those skilled in the art are considered to be encompassed by the preceding description and inventive scope.

TABLE 1

Summary of Representative Electrospray-Ion Mobility-Quadrupole Ion Trap Mass Spectrometer operating parameters.

| Operating Parameter | Mode of Operation | |
| --- | --- | --- |
| | Positive Mode | Negative Mode |
| ESI Source | | |
| ESI Spray Voltage (kV): | 12.5 | −12.5 |
| Flow Rate (µl/min): | 2.0 | 2.0 |
| Ion Mobility Spectrometer | | |
| Drift Tube Length (cm) | 17.6 | 17.6 |
| Drift Tube Temperature (° C.) | 185 | 185 |
| Ambient Pressure (Torr) | 690-710 | 690-711 |
| $N_2$ Counter Current Flow (mL/min) | 1000 | 1000 |
| Ion Mobility Entrance Screen (kV) | 9.5 | −9.5 |
| Ion Gate #1 Reference Potential (V) | 8010 | −8010 |
| Ion Gate #2 Reference Potential (V) | 1030 | −1030 |
| Ion Gate Pulsing Potential (V) | ±50 | ±50 |
| Ion Optics | | |
| Capillary Voltage (V): | 9.07 | 3.00 |
| Multipole 1 Offset (V): | −5.42 | 8.19 |
| Lens Voltage (V): | −67.55 | 61.70 |
| Multipole 2 Offset (V): | −11.49 | 12.73 |
| Entrance Lens Voltage (V): | −52.92 | 56.65 |
| Ion Trap DC Offset (V): | −10.18 | 9.80 |
| Ion Detection System | | |
| Dynode Voltage (kV): | −14.97 | −0.07 |
| Multiplier Voltage (V): | −1090.69 | −3.17 |
| Capillary Temp (° C.): | 185 | 185 |

The ion mobility control software was programmed using LabVIEW 6.1 (National Instruments, Austin, Tex.) and designed to interface with a PCI-6601 timing board (National Instruments, Austin, Tex.). The four 32-bit counters available on the timing board were used in tandem to produce a pulsing profile that drove the output signal of the gate pulsing electronics. The graphical interface allowed the user to define the ion gate pulse widths, $1^{st}$ and $2^{nd}$ ion gate delays, scan range, scan window, step resolution, and number of ion gate pulses per ion trap injection cycle.

The ion mobility timing control software governed (in some implementations, solely governed) the pulsing characteristics of the IMS system and was synchronized with the ion trap injection cycle. Ion mobility and ion trap data were collected using the ion trap Xcalibur suite of programs (Thermo Electron, San Jose, Calif.). In addition to specifying the m/z range to be scanned along with the ion trap injection time, the Xcalibur program allowed the user to define the number of µ-scans or ion trap scan averages included for each data point.

The selected mobility monitoring (SMM) mode of operation allows the user to filter a specific window of ions for mass analysis. The relevant parameters for this mode of operation include the $1^{st}$ ion gate pulse width, scan window, scan range, and number of ion gate pulses per ion trap injection cycle. At the beginning of the SMM experiment, the ion trap injection cycle initiates the pulsing sequence of the dual gate IMS system. The rising edge of the ion trap injection signal was synchronized with the pulsing of the first ion gate at the specified pulse width. The scan window governed the $2^{nd}$ ion gate pulse delay and width, whereas, the scan range determined the frequency at which the SMM experiment was repeated. The number of ion pulses allowed entry into the mass spectrometer was governed by the IMS scan range and the length of the ion trap injection cycle. For example, 40 SMM monitoring experiments could be completed with a SMM scan range of 25 ms and a 1000 ms ion trap injection time.

The dual gate scanning experiment allowed the ion populations' drift times to be determined through a successive series of stepped ion gate pulsing experiments. The pertinent operating variables for DGS include the $1^{st}$ and $2^{nd}$ ion gate pulse widths, $1^{st}$ ion gate delay (and in some embodiments, $2^{nd}$ gate delay), scan range, step resolution, and number of ion gate pulses per ion trap injection cycle. This experimental mode built upon the concept of the SMM mode by adding a stepping function to move the scan window through the user specified scan range. The width of the scan window in DGS was equal to the width of the $2^{nd}$ ion gate and the increment by which the $2^{nd}$ gate delay was advanced was equal to the step resolution, typically 0.05 ms. It should be noted that throughout the described experiments the width of the $1^{st}$ and $2^{nd}$ ion gate pulses were equal.

The parameters that govern the number of pulses per ion trap injection in SMM also applied to DGS; however, the number of ion gate pulses per data point had to be defined for each experiment. Expanding upon the example provided above, in order to attain 400 ion mobility gate pulses per point, 10 experimental cycles were completed before moving the $2^{nd}$ ion gate delay to the next increment. Compared to the traditional signal averaging mode used with ion mobility, experiments conducted using DGS were comparatively slow. Therefore, in the interest of efficiency, once a complete ion mobility scan was acquired, only a narrow range of drift times were examined for future SMM and DGS experiments.

Materials. The chemicals and materials used in the following Examples are as follows. The peptides demtide and bradykinin (Sigma, St. Louis, Mo.) along with cocaine (Alltech Associates, Inc., Deerfield, Ill.) were used without further purification. These compounds were examined in the positive mode using an electrospray solution of water, methanol, and acetic acid (50:49:1 by volume). The concentrations of cocaine, demtide, bradykinin, used to obtain mobility spectra were 32 pmol/µL, 20 pmol/µL, and 10 pmol/µL, respectively.

Dilutions from a 5 mM stock solution of the peptides were used for detection limit studies. Negative mode mobility and fragmentation spectra were obtained for melibiose (α-D-Gal-(1-6)-D-Glc) (Sigma, St. Louis, Mo.) and raffinose (α-D-Gal-(1-6)-α-D-Glc-(1-2)-β-D-Fru) (Supelco Inc., Bellefonte, Pa.) using a methanol-water mixture (90:10 by volume). The carbohydrate solution was a 4:1 molar ratio mixture of melibiose and raffinose with respective concentrations of 120 pmol/µL and 30 pmol/µL respectively. To ensure chlorine adduction in the negative mode 100 pmol of NaCl was added to each 1 mL of negative mode sample solution. Solvents used for these studies were of HPLC grade (J. T. Baker, Phillipsburg, N.J.) and used without further purification.

Particular exemplary preferred aspects.

Particular aspects provide a method for analysis of ion populations, comprising: obtaining an ion population; filtering and selecting the ion population or portions thereof using a low-field dual-gate low-field ion mobility spectrometer comprising a drift tube, the spectrometer operating at a pressure of at least 100 Torr, to provide for at least one low-field mobility-selected ion pulse; accumulating, during an ion trap injection cycle, the at least one mobility-selected ion pulse in an ion trap of a mass spectrometer, the ion trap in operative communication with the ion mobility spectrometer; and analyzing the accumulated mobility-selected ions by mass spectrometry.

Additional aspects provides a method for analysis of ion populations, comprising: obtaining an ion population; filtering and selecting the ion population or portions thereof using a dual-gate low-field ion mobility spectrometer comprising a drift tube, the spectrometer operating at least 100 Torr, to provide for at least one low-field mobility-selected ion pulse; introducing, during at least one introduction cycle, the at least one mobility-selected ion pulse into an ion-receiving portion of a high-field ion mobility spectrometer in operative communication with the low-field ion mobility spectrometer; and separating the introduced mobility-selected ions by high-filed ion mobility spectrometry to provide for high-field mobility selected ion populations. Certain aspects comprise introducing, prior to introducing the plurality of high-field mobility-selected ion populations into an ion-receiving portion of a mass spectrometer, accumulating, during an ion trap injection cycle, the plurality of high-field mobility-selected ion populations in an ion trap of a mass spectrometer, the ion trap in operative communication with the high-field ion mobility spectrometer.

Yet additional aspects provide a method for analysis of ion populations, comprising: obtaining an ion population; filtering and selecting the ion population or portions thereof using a first dual-gate low-field ion mobility spectrometer comprising a drift tube, the spectrometer operating at a pressure of at least 100 Torr, to provide at least one low-field mobility-selected ion pulse; and accumulating, during an ion trap injection cycle, a plurality of low-field mobility-selected ion pulses in an ion trap, the ion trap in operative communication with the output of the low-field ion mobility spectrometer to provide for selected accumulated ions. Particular aspects further comprise introducing the selected accumulated ions into an ion-receiving portion of a second low-field ion mobility spectrometer in operative communication with the ion trap; and separating the introduced selected accumulated ions by further low-field ion mobility spectrometry to provide for further mobility selected ions. In particular embodiments, the second low-field ion mobility spectrometer is a non-dual gate spectrometer operating at less than about 100 Torr.

Further aspects provide an apparatus for analysis of ion populations, comprising: a dual-gate low-field ion mobility spectrometer comprising a drift tube, two ion gates and controlling means to enable the gates to work in tandem to select ion populations based upon their drift times, the spectrometer suitable to operate at a pressure of at least 100 Torr to filter and select an ion populations to provide for mobility-selected ions; and an ion trap mass spectrometer, or a high-field ion mobility spectrometer, in operative communication with the dual gate low-field ion mobility spectrometer to further filter and select ion populations. In particular aspects, the high field ion mobility spectrometer is that of a FAIMS system. Certain aspects that comprise a high-field ion mobility spectrometer (e.g., FAIMS system), further comprise a mass spectrometer in operative communication with the output of the high-field ion mobility spectrometer to further filter and select ion populations. Certain aspects that comprise an ion trap mass spectrometer further comprise a low-field ion mobility spectrometer in operative communication with the output of the ion trap mass spectrometer to further filter and select ion populations.

In certain aspects of the above-described methods and apparatus, the dual-gate ion mobility spectrometer comprises gates selected from the gate group consisting of Tyndall, Bradbury-Nielson, electric potential well, an effective gate comprising an ion pulse from an ionization source, and combinations thereof, along with controlling means to enable the gates to work in tandem to select ion populations based upon their drift times. Preferably, the dual-gate ion mobility spectrometer comprises two Bradbury-Nielson gates and controlling means to enable the gates to work in tandem to select ion populations based upon their drift times. In particular embodiments, the parameters settable by the controlling means are selected from the group consisting of: a first ion gate pulse width; a scan window governing a second ion gate pulse delay and width, a scan range, an ion trap injection cycle time, a number of ion gate pulses per ion trap injection cycle, and combinations thereof. In particular aspects, the ion trap comprises at least one ion trap selected from the group consisting of a quadrupole ion trap, a linear ion trap, and an ion cyclotron resonance cell. In certain aspects, the ion trap comprises a quadrupole ion trap. In particular embodiments, separating and filtering the ion population, or portions thereof, using the dual-gate ion mobility spectrometer comprises operative coordination of one or more settable parameters selected from the group consisting of: a first ion gate pulse width; a scan window governing a second ion gate pulse delay and width, a scan range, an ion trap injection cycle time, and a number of ion gate pulses per ion trap injection cycle. Particular aspects further comprise, prior to separating and filtering the ion population, determining a drift time for a desired ion or ion population. In certain aspects, obtaining an ion population comprises use of at least one ion source selected from the group consisting of electrospray ionization (ESI) unit, radioactive source, corona discharge, ionization, atmospheric pressure photoionization, and matrix assisted laser desorption. Preferably, obtaining an ion population comprises use of an electrospray ionization (ESI) unit. In certain aspects, the electrospray ionization unit is positioned off-axis with respect to the axis of the drift tube of the dual-gate ion mobility spectrometer. In particular embodiments, the off-axis orientation is about 45 degrees off the axis of the drift tube. In certain aspects, filtering and selecting the ion population or portions thereof is of, or comprises filtering and selecting of positive ions. In certain aspects, filtering and selecting the ion population or portions thereof is of, or comprises filtering and selecting of negative ions.

EXAMPLES

Example 1

Measurement of Automatic Gain Control (AGC) on the Observed Intensities of Mobility Selected Demptide $[M+2H]^{2+}$ Ions By controlling the level of ions introduced and collected in the ion trap, automatic gain control (AGC) minimizes the effect of space-charging (March and Todd, *Practical Aspects of Ion Trap Mass Spectrometry*, Vol. 1, CRC Press, New York, N.Y., p. 10-11, 1995). Increases in linear dynamic range and spectral resolution are the primary benefits of AGC, which in turn have resulted in a large expansion in the application of QIT MS as an analytical technique. During normal QIT operation, the injection time of the electrosprayed ions is varied depending upon their abundance relative to a pre-defined target ion concentration.

When selected, the AGC feature performs a "pre-scan" of ions prior to initiating a mass scan. This "pre-scan" functions to estimate the number of ions entering the trap at a given time and adjusts the accumulation time according to the target ion concentration. An unfortunate consequence of this mode of ion injection and ejection is the loss of ions available for analysis. Given the low duty cycle of the ion mobility experiment, minimizing losses is paramount.

Figure 3A:
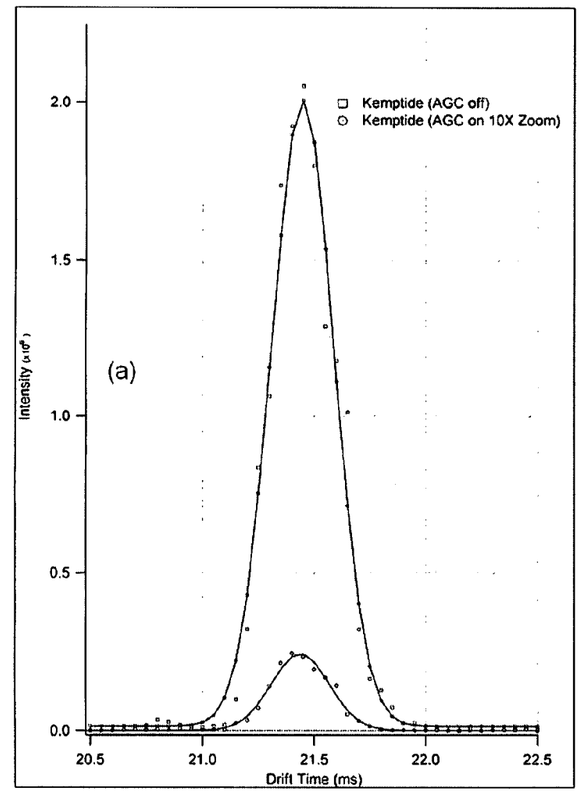
FIG. 3a illustrates, according to particular exemplary embodiments, the effect of automatic gain control (AGC) on the observed intensities of mobility selected demptide $[M+2H]^{+2}$ ions. The spectra shown contrast the observed demtide signal with and without AGC. The ion mobility peak obtained with AGC has been enhanced 10-fold for comparison.
Figure 3B:
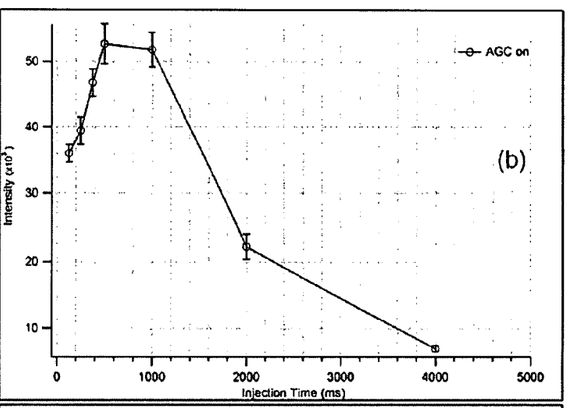
FIG. 3b illustrates, according to particular exemplary embodiments, the effect of automatic gain control (AGC) on the observed intensities of mobility selected demptide $[M+2H]^{+2}$ ions. The plot illustrates the average ion current observed for 500 ion mobility pulses as a function of ion injection time with AGC.
Figure 3C:
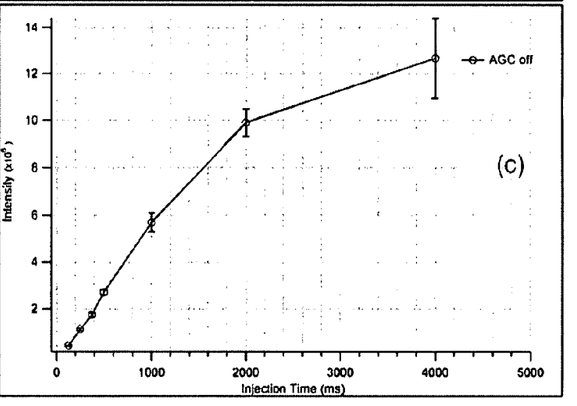
FIG. 3c illustrates, according to particular exemplary embodiments, the effect of automatic gain control (AGC) on the observed intensities of mobility selected demptide $[M+2H]^{+2}$ ions. The plot illustrates the average ion current observed for 500 ion mobility pulses as a function of ion injection time without AGC.

The mobility spectra and plots in FIG. 3 demonstrate the effect of AGC on the intensity and trapping efficiency when the DG-IMS was used in conjunction with the QIT. FIG. 3a illustrates the effect of AGC on the intensity of the demtide $[M+2H]^{2+}$ ion mobility peaks, where each data point is the result of 500, 0.3 ms wide ion mobility pulses acquired in the DGS mode. For the purposes of display, the mobility trace acquired with AGC was enhanced by a factor of 10. Additionally, the observed mobility peaks arise from the best fit of the acquired data points. Compared to ion mobility data collected with AGC, spectra obtained without AGC displayed an 8-fold increase in the signal-to-noise ratio (SNR). This large difference in SNR results from the mechanism by which AGC monitors the level of ions entering the trap. FIGS. 3b and 3c compare the demtide $[M+2H]^{2+}$ ion intensity against the ion trap injection time. Each data point within FIGS. 3b and 3c resulted from averaging 500 ion gate pulses of a SMM experiment. Data collected with AGC (FIG. 3b) exhibits a marked decrease in the ability to trap mobility selected ions at larger injection times.

In order to maintain a constant ion injection time while utilizing AGC, the target ion concentration was set unrealistically high and the injection time specified in the Xcalibur software. It should be noted this circumvention did not prevent the QIT from performing a pre-scan which was responsible for the apparent reduction in trapping efficiency at higher accumulation times. Combined with the results shown in FIG. 3a, the data from conducting the SMM experiment without AGC (FIG. 3c) demonstrates the ability of the DG-IM-QIT to effectively concentrate ions. Again given the low duty cycle of the ion mobility experiment, the number of ions being injected into the QIT was insufficient to produce the observed m/z shifts and spectral degradation associated with Coulombic repulsion. This effect would undoubtedly be observed with longer accumulation times; however, the commercial nature of the LCQ Deca limited the range of injection times available for experimentation. Due to the SNR and trapping advantage observed without AGC, this mode of operation was used for the remainder of the described experiments and Examples, unless stated otherwise.

Example 2

Figure 4:
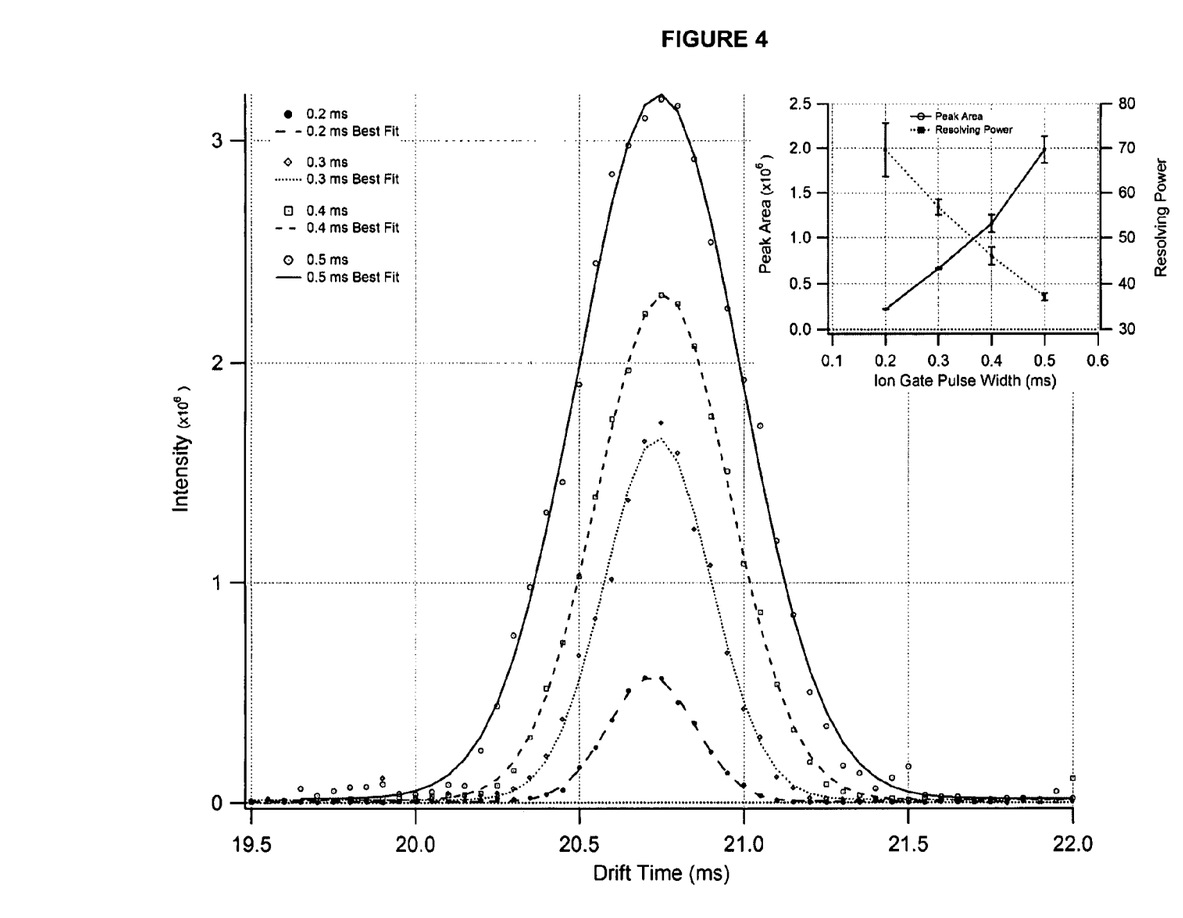
FIG. 4 illustrates, according to particular exemplary embodiments, the variation of resolving power and peak area as a function of ion gate pulse width for a 32 pmol/µL solution of cocaine. The mobility spectra shown were obtained using the dual gate scanning mode with the $1^{st}$ and $2^{nd}$ ion gate pulse widths being equal.

Measurement of the Variation of Resolving Power and Peak Area as a Function of Ion Gate Pulse Width The ion mobility spectra shown in FIG. 4 illustrate the effect of ion gate pulse width on the observed peak area and resolving power for a 32 pmol/μL solution of cocaine. For the mobility spectra displayed in FIG. 4 the widths of the $1^{st}$ and $2^{nd}$ ion gates varied from 0.2 to 0.5 ms. Attempts were made to acquire data at ion gate pulse widths below 0.2 ms, however, no ion signal was observed. Commonly defined as ion drift time divided by the peak width at half height, the ion mobility resolving power observed for cocaine using the DG-IM-QIT instrument ranged from 70±6 to 37±1. These values on average were within 5% of the theoretical maximum resolution power[40]. The inset plot located in FIG. 4 shows the inverse relation between resolving power and peak area. While the intersection of the peak area and resolving power trends corresponded to an ion gate pulse width of ~0.36, in order to err on the side of improved resolving power, peak widths of 0.3 ms were used for further experiments unless otherwise noted.

Example 3

Measurement of Detection Limits and Linear Dynamic Range

Figure 5A:
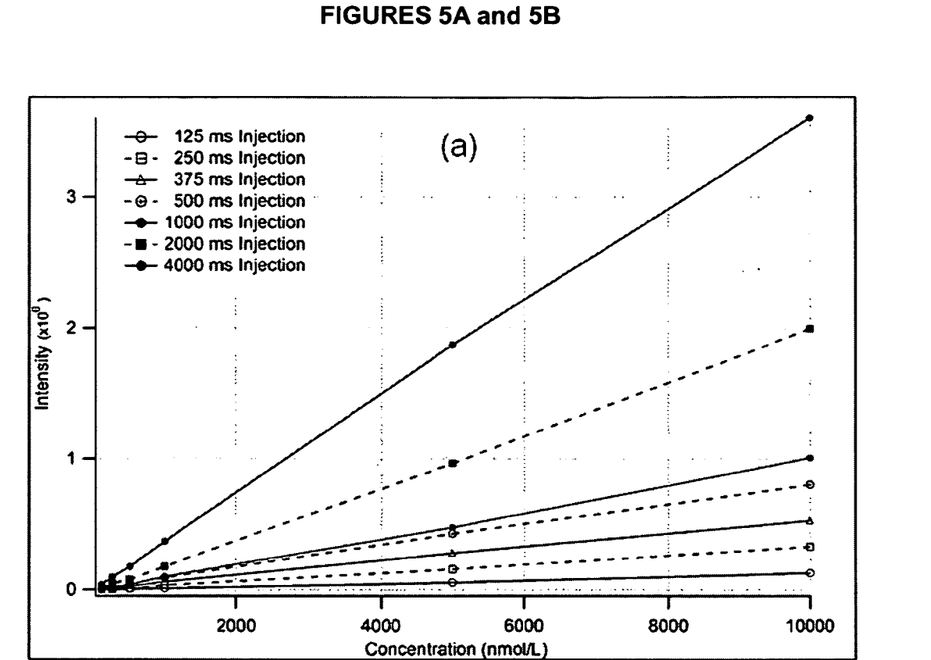
FIG. 5a shows, according to particular exemplary embodiments, a plot representing the calibration curves for the $[M+2H]^{+2}$ ion of demtide at varying ion trap injection times. The measurement relative standard deviation (RSD) for each concentration is compared to the injection time in Plot 5b.

To assess the limits of detection (LOD) and dynamic range of the DG-IM-QIT, calibration curves were constructed for the demtide $[M+2H]^{2+}$ ion collected at different ion trap injection times (FIG. 5a). Each data point represents the average of a one minute SMM monitoring experiment. Because the ion trap scan cycle requires a period of reset prior to beginning the next scan, varying the injection time also changes the number of injection cycles performed during a fixed time period. Despite taking steps to normalize for the number of scan cycles and ion mobility pulses, the 4000 ms injection time possessed the greatest slope and analytical sensitivity (Skoog et al., *Principles of Instrumental Analysis*, $5^{th}$ ed., Saunders College Publishing, Philadelphia, Pa., p. 13, 1998). The diminished slopes observed at smaller injection times resulted directly from the reduced number of ions available for analysis. While this plot, combined with the results shown in FIG. 3c, may suggest the maximum injection time is most favorable, practical experience suggests otherwise. Operation at extended accumulation times may become problematic as each data point within a mobility spectrum was the result of numerous ion mobility gate pulses and QIT scan averages. In the event of ion gate leakage or gate depletion the number of ions pulsed into the QIT may become abnormally high or low (Chen et al., *Anal. Chim. Acta* 334(1-2):75-84, 1996; Knorr et al., *Anal. Chem.* 57(2):402-406, 1985). If the injection time is sufficiently high and the number of scan averages per mobility point low, an erroneous reading resulting from one scan may distort the recorded spectrum. Therefore, a balance must be realized between the number of ion gate pulses and QIT injection cycles represented within each data point. For ion mobility scan times of 25 ms, QIT injection times of 1000 ms were found to consistently reproduce spectra while minimizing averaging defects.

Figure 5B:
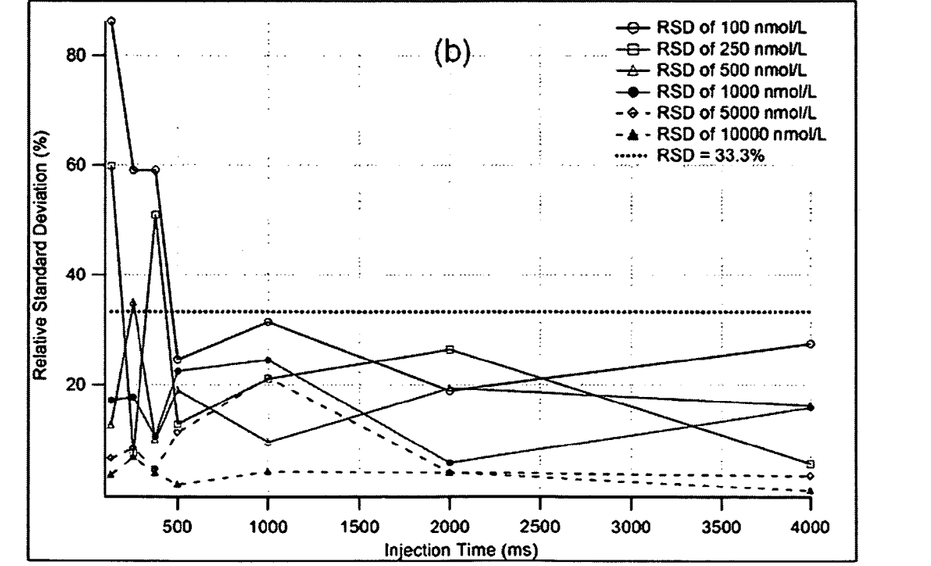
FIG. 5b shows, according to particular exemplary embodiments, the measurement relative standard deviation (RSD) for each concentration. The horizontal dotted line (RSD=33.3%) is the level at which each measurement must not exceed otherwise the value becomes statistically uncertain. Plot 5b indicates a minimum injection time of 500 ms was necessary to detect demtide at the 100 nmol/L concentration.

The relative standard deviation (RSD) of each point in FIG. 5a is plotted as a function of peptide concentration and injection time in FIG. 5b. Because the concentration of ions during an ion mobility experiment is significantly reduced (~$10^3$) compared to a traditional MS experiment, the threshold level for detection using a MS based detector must be reached in order for a signal to register. As this level may not be attained during the course of certain IMS experiments, an alternative to measuring the standard deviation of the blank must was used to determine detection limits. The horizontal dashed line located in FIG. 5b represents the level at which the RSD of the measurements equals 33.3%. At this level the measurement is statistically equivalent to three times the standard deviation of the blank. This description is consistent with the International Union of Pure and Applied Chemistry (IUPAC) guidelines regarding limits of detection (Gilfrich and Birks, *Anal. Chem.* 56(1):77-79, 1984). Interpretation of FIG. 5b using this definition suggests an injection time of 500 ms was necessary to statistically assign a demtide LOD of 100 nmol/L. Deviation from a linear dynamic range was observed above demtide concentrations above 75 µmol/L.

Example 4

Figure 6:
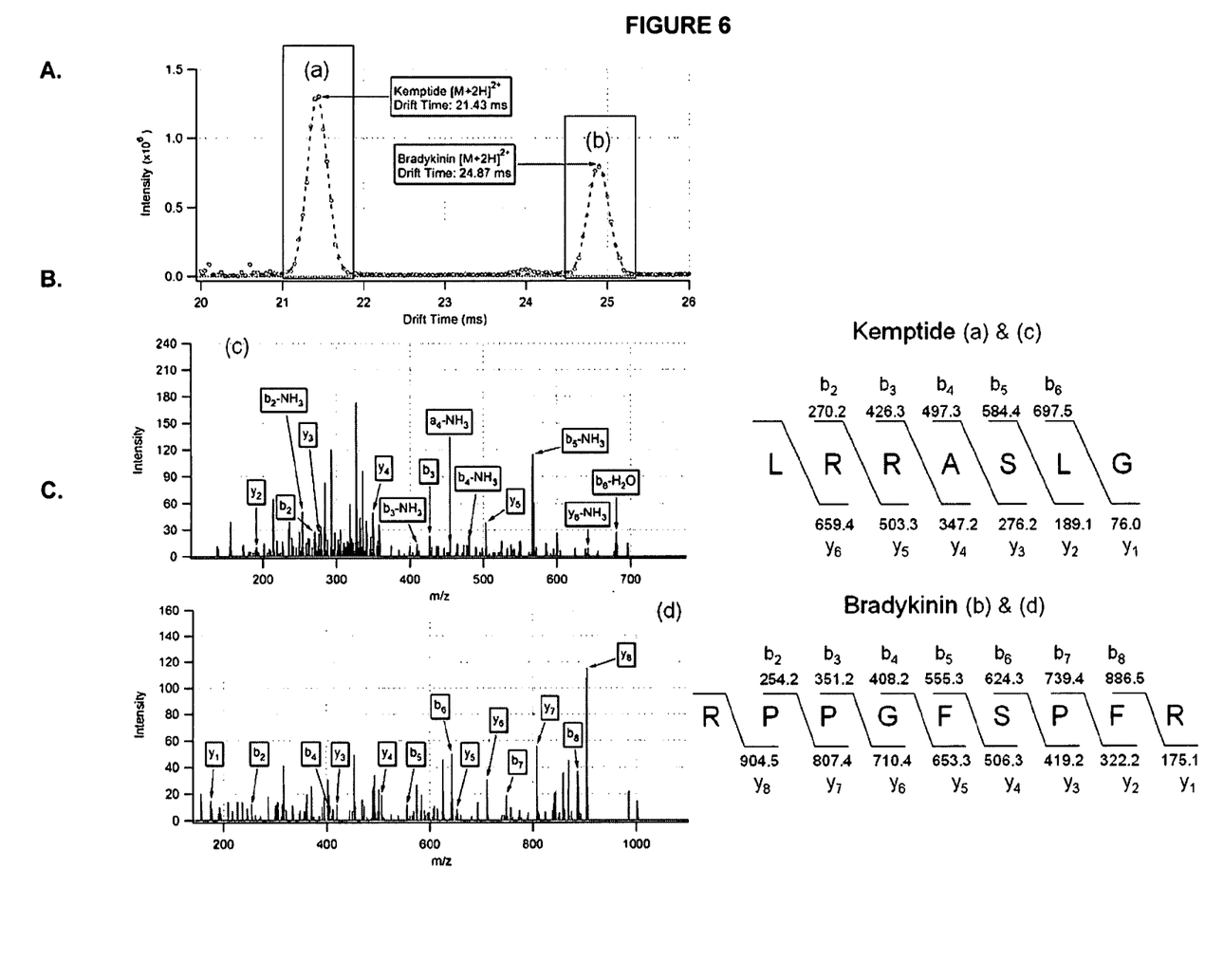
FIG. 6a shows, according to particular exemplary embodiments, two mobility peaks labeled (a) and (b) corresponding to the $[M+2H]^{+2}$ ions of demtide and bradykinin respectively.
FIG. 6b shows, according to particular exemplary embodiments, de novo sequencing information acquired using a 40 picomolar concentration of demtide.
FIG. 6c shows de novo sequencing information acquired using a 20 pico molar concentration of bradykinin.

Mobility Filtration and Selective Fragmentation of Melibiose and Raffinose in Positive Mode The [M+2H]$^{+2}$ ions of bradykinin and demtide were identified from a simple mixture based upon their reduced mobility values and MS fragmentation patterns. The ion mobility spectrum shown in FIG. 6 was acquired using the DGS mode with a scan window of 20-26 ms and step resolution of 0.05 ms. Additionally, each data point resulted from the average of twenty 1000 ms µ-scans for a total of 600 ion mobility pulses per point. The reduced mobility values for the demtide [M+2H]$^{+2}$ (Peak (a) in FIG. 6a) and bradykinin [M+2H]$^{+2}$ (Peak (b) in FIG. 6a) ions compare well with the available literature[12] and were 1.15 cm$^2$Vs and 0.99 cm$^2$Vs respectively. Once the peptide drift times were determined SMM experiments were conducted for 1 minute to acquire MS/MS fragmentation data. It should be noted that in order to obtain MS/MS data the AGC feature was employed. Displayed in FIG. 6c and FIG. 6d is the complete de novo sequencing of 40 pmols of demtide [M+2H]$^{+2}$ and 20 pmols of bradykinin [M+2H]$^{+2}$. The data shown in FIGS. 6a, 6b, and 6c clearly demonstrate the ability of the DG-IM-QIT to perform MS/MS experiment on mobility selected ions.

Example 5

Figure 7:
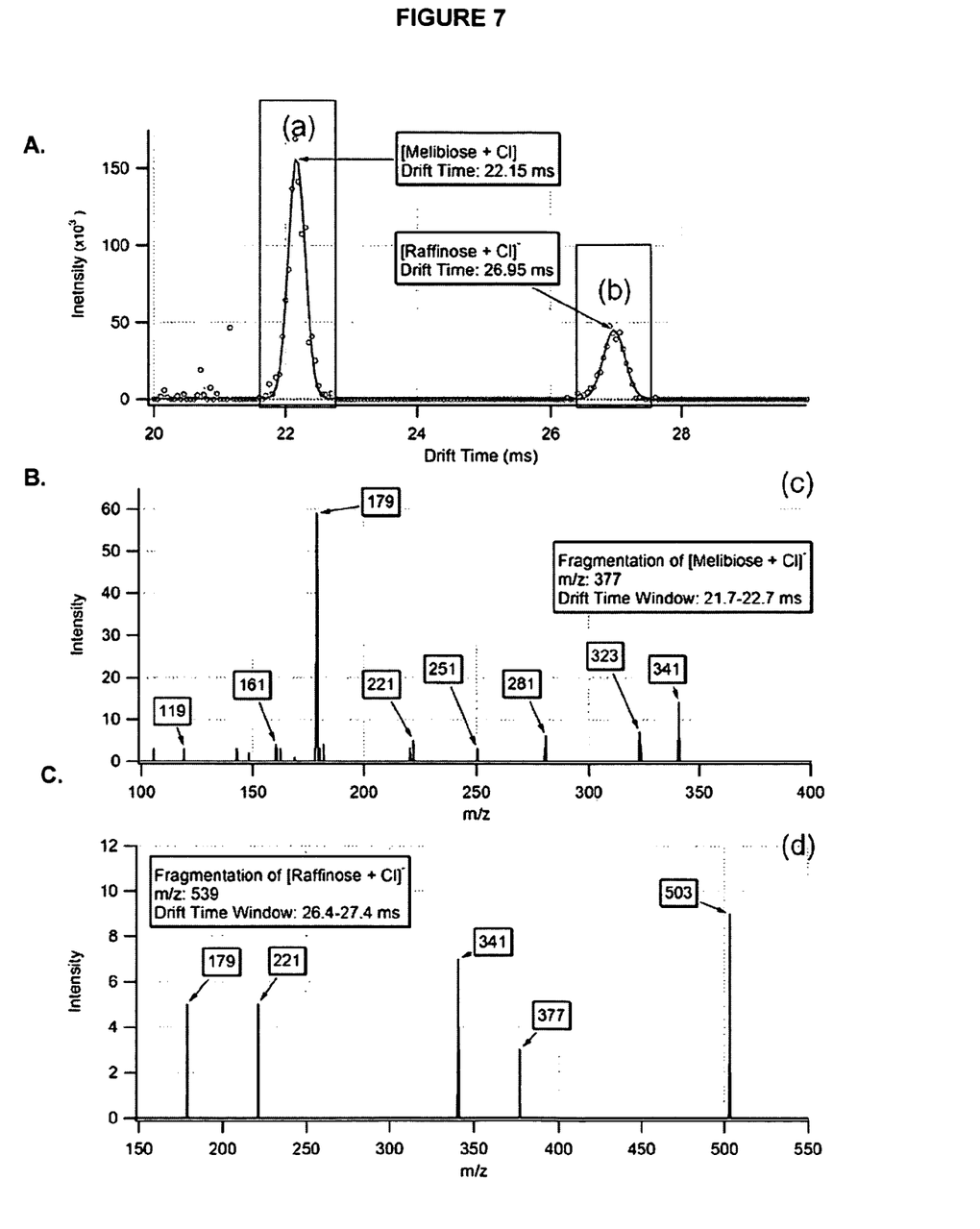
FIG. 7a shows, according to particular exemplary embodiments, the mobility of selected chlorine adducts of melibiose and raffinose. The fragmentation peaks observed correspond to the characteristic cleavage patterns observed for carbohydrates.
FIG. 7b shows, according to particular exemplary embodiments, the fragmentation of melibiose. The fragmentation peaks observed correspond to the characteristic cleavage patterns observed for carbohydrates.
FIG. 7c shows, according to particular exemplary embodiments, the fragmentation of raffinose. The fragmentation peaks observed correspond to the characteristic cleavage patterns observed for carbohydrates.

Mobility Filtration and Selective Fragmentation of Melibiose and Raffinose in Negative Mode To further explore the mobility filtration and selective fragmentation capabilities of the DG-IM-QIT two carbohydrates, melibiose and raffinose were examined in the negative mode. As with the positive mixture of peptides, the DGS mode was used to determine the drift times of the selected carbohydrates followed by SMM and MS/MS fragmentation. Initial results indicated the small presence of a chlorine adduct in the mass spectrum when electrospraying the solution mixture. Removal of this adduct proved exceedingly difficult, therefore, in order to consolidate the ion signal into a single peak ~100 pmol of NaCl were added to each 1 mL of sample solution. The mobility peaks corresponding to the negative chlorine adduct of melibiose and raffinose are labeled (a) and (b) in FIG. 7a. Their corresponding reduced mobility values were 1.10 cm$^2$Vs and 0.90 cm$^2$/Vs respectively. Selective mobility monitoring filtration and MS/MS fragmentation of the carbohydrate chlorine adducts for 3 minutes produced the MS/MS spectra shown in FIG. 7c and FIG. 7d. The mass spectrum in FIG. 7c displays the product ions originating from the SMM experiment for the 377 m/z melibiose chlorine adduct. Aside from the 341 m/z ion (M−H)⁻ the remaining labeled fragmentation peaks were assigned to the characteristic carbohydrate cleavage patterns according to the processes outlined by Domon and Costello[45]. Further, MS$^3$ fragmentation (data not shown) of the 341 m/z ion isolated from the chlorine adduct of raffinose produced spectra containing the ions found in FIG. 7c. As raffinose contains the melibiose moiety this observation was not unforeseen, however, does provide evidence for complex MS″ experiments being conducted on mobility selected ions.

The invention claimed is:

1. A method for analysis of ion populations, comprising: obtaining an ion population; filtering and selecting the ion population or portions thereof using a dual-gate low-field ion mobility spectrometer comprising a drift tube, the spectrometer operating at a pressure of at least 100 Torr, to provide for at least one low-field mobility-selected ion pulse; accumulating, during an ion trap injection cycle, the at least one mobility-selected ion pulse in an ion trap of a mass spectrometer, the ion trap in operative communication with the ion mobility spectrometer; and analyzing the accumulated mobility-selected ions by mass spectrometry.

2. The method of claim 1, wherein the dual-gate ion mobility spectrometer comprises gates selected from the gate group consisting of Tyndall, Bradbury-Nielson, electric potential well, an effective gate comprising an ion pulse from an ionization source, and combinations thereof, along with controlling means to enable the gates to work in tandem to select ion populations based upon their drift times.

3. The method of claim 2, wherein the dual-gate ion mobility spectrometer comprises two Bradbury-Nielson gates and controlling means to enable the gates to work in tandem to select ion populations based upon their drift times.

4. The method of claim 2, wherein parameters settable by the controlling means are selected from the group consisting of: a first ion gate pulse width; a scan window governing a second ion gate pulse delay and width, a scan range, an ion trap injection cycle time, a number of ion gate pulses per ion trap injection cycle, and combinations thereof.

5. The method of claim 1, wherein the ion trap comprises at least one ion trap selected from the group consisting of a quadrupole ion trap, a linear ion trap, and an ion cyclotron resonance cell.

6. The method of claim 1, wherein the ion trap comprises a quadrupole ion trap.

7. The method of claim 1, wherein separating and filtering the ion population, or portions thereof, using the dual-gate ion mobility spectrometer comprises operative coordination of one or more settable parameters selected from the group consisting of: a first ion gate pulse width; a scan window governing a second ion gate pulse delay and width, a scan range, an ion trap injection cycle time, and a number of ion gate pulses per ion trap injection cycle.

8. The method of claim 1, further comprising, prior to separating and filtering the ion population, determining a drift time for a desired ion or ion population.

9. The method of claim 1, wherein obtaining an ion population comprises use of at least one ion source selected from the group consisting of electrospray ionization (ESI) unit, radioactive source, corona discharge, ionization, atmospheric pressure photoionization, and matrix assisted laser desorption.

10. The method of claim 9, wherein obtaining an ion population comprises use of an electrospray ionization (ESI) unit.

11. The method of claim 10, wherein the electrospray ionization unit is positioned off-axis with respect to the axis of the drift tube of the dual-gate ion mobility spectrometer.

12. The method of claim 11, wherein the off-axis orientation is about 45 degrees off the axis of the drift tube.

13. The method of claim 12, wherein filtering and selecting the ion population or portions thereof is of positive ions.

14. The method of claim 1, wherein filtering and selecting the ion population or portions thereof is of negative ions.

15. A method of analysis of ion populations, comprising:
separating ions using dual gate low-field ion mobility spectrometry at atmospheric pressure or higher pressure;
filtering the ions to select specific ions;

accumulating the selected ions in an accumulation means; and analyzing the accumulated ions by mass spectrometry or ion mobility means.

16. A apparatus for analysis of ion populations, comprising:
a dual-gate low-field ion mobility spectrometer comprising a drift tube, two ion gates and controlling means to enable the gates to work in tandem to select ion populations based upon their drift times, the spectrometer suitable to operate at a pressure of at least 100 Torr to filter and select an ion populations to provide for mobility-selected ions;
an ion trap mass spectrometer, or a high-field ion mobility spectrometer, in operative communication with the dual gate low-field ion mobility spectrometer to further filter and select ion populations.

17. The apparatus of claim 16, wherein the dual-gate ion mobility spectrometer comprises gates selected from the gate group consisting of Tyndall, Bradbury-Nielson, electric potential well, an effective gate comprising an ion pulse from an ionization source, and combinations thereof, along with controlling means to enable the gates to work in tandem to select ion populations based upon their drift times.

18. The apparatus of claim 17, wherein the dual-gate ion mobility spectrometer comprises two Bradbury-Nielson gates and controlling means to enable the gates to work in tandem to select ion populations based upon their drift times.

19. The apparatus of claim 16, wherein the ion trap comprises at least one ion trap selected from the group consisting of a quadrupole ion trap, a linear ion trap, and an ion cyclotron resonance cell.

20. The apparatus of claim 16, wherein the ion trap comprises a quadrupole ion trap.

21. The apparatus of claim 16, further comprising an ion source selected from the group consisting of electrospray ionization (ESI) unit, radioactive source, corona discharge, ionization, atmospheric pressure photoionization, and matrix assisted laser desorption suitable in operation to provide for an ion population.

22. The apparatus of claim 21, wherein the ion source comprises an electrospray ionization (ESI) unit.

23. The apparatus of claim 21, wherein the electrospray ionization unit is positionable off-axis with respect to the axis of the drift tube of the dual-gate ion mobility spectrometer.

24. The apparatus of claim 23, wherein the electrospray ionization unit is positionable at about 45 degrees off the axis of the drift tube.

25. The apparatus of claim 16, wherein parameters settable by the controlling means are selected from the group consisting of: a first ion gate pulse width; a scan window governing a second ion gate pulse delay and width, a scan range, an ion trap injection cycle time, a number of ion gate pulses per ion trap injection cycle, and combinations thereof.

26. The apparatus of claim 16, comprising software and electronic means operative therewith for determining ion drift time by using a DGS mode, and for filtering ions, based on the drift time, using a SMM mode.

27. The apparatus of claim 16, wherein the high field ion mobility spectrometer is that of a FAIMS system.

28. The apparatus of claim 27, wherein parameters settable by the controlling means are selected from the group consisting of: a first ion gate pulse width; a scan window governing a second ion gate pulse delay and width, a scan range, a number of ion gate pulses per injection cycle, a compensation voltage, a compensation voltage sweep rate, a compensation voltage hold time and combinations thereof.

29. The apparatus of claim 27, further comprising a mass spectrometer in operative communication with the output of the high-field ion mobility spectrometer to further filter and select ion populations.

30. The apparatus of claim 29, wherein the mass spectrometer comprises at least one mass spectrometer selected from the group consisting of single, double or triple Quadrupole, Quadrupole Ion Trap (QIT), Linear Ion Trap (LIT), fourier transform mass spectrometer (FTMS), and Time-of-Flight (TOF).

31. The apparatus of claim 16, further comprising a mass spectrometer in operative communication with the output of the high-field ion mobility spectrometer to further filter and select ion populations.

32. The apparatus of claim 31, wherein the mass spectrometer comprises at least one mass spectrometer selected from the group consisting of single, double or triple Quadrupole, Quadrupole Ion Trap (QIT), Linear Ion Trap (LIT), fourier transform mass spectrometer (FTMS), and Time-of-Flight (TOF).

33. The apparatus of claim 16, further comprising a low-field ion mobility spectrometer in operative communication with the output of the ion trap mass spectrometer to further filter and select ion populations.

34. A method for analysis of ion populations, comprising:
obtaining an ion population;
filtering and selecting the ion population or portions thereof using a dual-gate low-field ion mobility spectrometer comprising a drift tube, the spectrometer operating at least 100 Torr, to provide for at least one low-field mobility-selected ion pulse;
introducing, during at least one introduction cycle, the at least one mobility-selected ion pulse into an ion-receiving portion of a high-field ion mobility spectrometer in operative communication with the low-field ion mobility spectrometer; and
separating the introduced mobility-selected ions by high-filed ion mobility spectrometry to provide for high-field mobility selected ion populations.

35. The method of claim 34, wherein the dual-gate ion mobility spectrometer comprises gates selected from the gate group consisting of Tyndall, Bradbury-Nielson, electric potential well, an effective gate comprising an ion pulse from an ionization source, and combinations thereof, along with controlling means to enable the gates to work in tandem to select ion populations based upon their drift times.

36. The method of claim 35, wherein the dual-gate ion mobility spectrometer comprises two Bradbury-Nielson gates and controlling means to enable the gates to work in tandem to select ion populations based upon their drift times.

37. The method of claim 35, wherein parameters settable by the controlling means are selected from the group consisting of: a first ion gate pulse width; a scan window governing a second ion gate pulse delay and width, a scan range, and combinations thereof.

38. The method of claim 34, wherein the high-field ion mobility spectrometer is that of a FAIMS system.

39. The method of claim 34, wherein separating and filtering the ion population, or portions thereof, using the dual-gate ion mobility spectrometer comprises operative coordination of one or more settable parameters selected from the group consisting of: a first ion gate pulse width; a scan window governing a second ion gate pulse delay and width, and a scan range.

40. The method of claim 34, further comprising, prior to separating and filtering the ion population, determining a drift time for a desired ion or ion population.

41. The method of claim 34, wherein obtaining an ion population comprises use of at least one ion source selected from the group consisting of electrospray ionization (ESI) unit, radioactive source, corona discharge, ionization, atmospheric pressure photoionization, and matrix assisted laser desorption.

42. The method of claim 41, wherein obtaining an ion population comprises use of an electrospray ionization (ESI) unit.

43. The method of claim 42, wherein the electrospray ionization unit is positioned off-axis with respect to the axis of the drift tube of the dual-gate ion mobility spectrometer.

44. The method of claim 43, wherein the off-axis orientation is about 45 degrees off the axis of the drift tube.

45. The method of claim 34, wherein filtering and selecting the ion population or portions thereof is of positive ions.

46. The method of claim 34, wherein filtering and selecting the ion population or portions thereof is of negative ions.

47. The method of claim 34, further comprising:
introducing, at least one high-field mobility-selected ion population into an ion-receiving portion of a mass spectrometer in operative communication with the high-field ion mobility spectrometer; and
analyzing the mobility-selected ions by mass spectrometry.

48. The method of claim 47, further comprising:
introducing, prior to introducing the plurality of high-field mobility-selected ion populations into an ion-receiving portion of a mass spectrometer, accumulating, during an ion trap injection cycle, the plurality of high-field mobility-selected ion populations in an ion trap of a mass spectrometer, the ion trap in operative communication with the high-field ion mobility spectrometer.

49. The method of claim 47, wherein the mass spectrometer comprises at least one mass spectrometer selected from the group consisting of single, double or triple Quadrupole, Quadrupole Ion Trap (QIT), Linear Ion Trap (LIT), fourier transform mass spectrometer (FTMS), and Time-of-Flight (TOF).

50. The method of claim 49, wherein the mass spectrometer comprises a Quadrupole Ion Trap (QIT) mass spectrometer.

51. A method for analysis of ion populations, comprising:
obtaining an ion population;
filtering and selecting the ion population or portions thereof using a first dual-gate low-field ion mobility spectrometer comprising a drift tube, the spectrometer operating at a pressure of at least 100 Torr, to provide at least one low-field mobility-selected ion pulse; and
accumulating, during an ion trap injection cycle, a plurality of low-field mobility-selected ion pulses in an ion trap, the ion trap in operative communication with the output of the low-field ion mobility spectrometer to provide for selected accumulated ions.

52. The method of claim 51, wherein the first low-field dual-gate ion mobility spectrometer comprises gates selected from the gate group consisting of Tyndall, Bradbury-Nielson, electric potential well, an effective gate comprising an ion pulse from an ionization source, and combinations thereof, along with controlling means to enable the gates to work in tandem to select ion populations based upon their drift times.

53. The method of claim 52, wherein the first dual-gate ion mobility spectrometer comprises two Bradbury-Nielson gates and controlling means to enable the gates to work in tandem to select ion populations based upon their drift times.

54. The method of claim 52, wherein parameters settable by the controlling means are selected from the group consisting of: a first ion gate pulse width; a scan window governing a second ion gate pulse delay and width, a scan range, an ion trap injection cycle time, a number of ion gate pulses per ion trap injection cycle, and combinations thereof.

55. The method of claim 51, wherein the ion trap comprises at least one ion trap selected from the group consisting of that of a quadrupole ion trap, a linear ion trap, and an ion cyclotron resonance cell.

56. The method of claim 51, wherein the ion trap comprises a quadrupole ion trap.

57. The method of claim 51, wherein separating and filtering the ion population, or portions thereof, using the first dual-gate ion mobility spectrometer comprises operative coordination of one or more settable parameters selected from the group consisting of: a first ion gate pulse width; a scan window governing a second ion gate pulse delay and width, a scan range, an ion trap injection cycle time, and a number of ion gate pulses per ion trap injection cycle.

58. The method of claim 51, further comprising, prior to separating and filtering the ion population, determining a drift time for a desired ion or ion population.

59. The method of claim 51, wherein obtaining an ion population comprises use of at least one ion source selected from the group consisting of electrospray ionization (ESI) unit, radioactive source, corona discharge, ionization, atmospheric pressure photoionization and matrix assisted laser desorption.

60. The method of claim 59, wherein obtaining an ion population comprises use of an electrospray ionization (ESI) unit.

61. The method of claim 60, wherein the electrospray ionization unit is positioned off-axis with respect to the axis of the drift tube of the dual-gate ion mobility spectrometer.

62. The method of claim 61, wherein the off-axis orientation is about 45 degrees off the axis of the drift tube.

63. The method of claim 51, wherein filtering and selecting the ion population or portions thereof is of positive ions.

64. The method of claim 51, wherein filtering and selecting the ion population or portions thereof is of negative ions.

65. The method of claim 51, further comprising:
Introducing the selected accumulated ions into an ion-receiving portion of a second low-field ion mobility spectrometer in operative communication with the ion trap; and
separating the introduced selected accumulated ions by further low-field ion mobility spectrometry to provide for further mobility selected ions.

66. The method of claim 65, wherein the second low-field ion mobility spectrometer is a non-dual gate spectrometer operating at less than about 100 Torr.

* * * * *